United States Patent [19]

Hoeschele

[11] Patent Number: 5,049,686

[45] Date of Patent: Sep. 17, 1991

[54] LARGE-RING DIAMINE PLATINUM(II) AND PLATINUM(IV) CHELATES

[75] Inventor: James D. Hoeschele, Canton, Mich.

[73] Assignee: Warner-Lambert Company, Morris Plains, N.J.

[21] Appl. No.: 406,646

[22] Filed: Sep. 13, 1989

[51] Int. Cl.$^5$ ...................... C07F 15/00; A61K 33/00
[52] U.S. Cl. .................................... 556/137; 556/136
[58] Field of Search ........................ 556/137, 40, 41; 514/492

[56] References Cited

U.S. PATENT DOCUMENTS 4,477,387  10/1984  Kidani et al. .
4,864,043  9/1989  Nowatari et al. .................... 556/40

FOREIGN PATENT DOCUMENTS 0282672  9/1988  European Pat. Off. ............ 556/137

Primary Examiner—Arthur C. Prescott
Attorney, Agent, or Firm—Francis J. Tinney

[57] ABSTRACT

Novel large-ring diamine platinum(II) and platinum-(IV) complexes which are useful in inhibiting the growth of malignant neoplasms, as well as novel pharmaceutical compositions and methods of use, as well as processes for their manufacture are herein described.

13 Claims, No Drawings

LARGE-RING DIAMINE PLATINUM(II) AND PLATINUM(IV) CHELATES

BACKGROUND OF THE INVENTION

The present invention relates to novel large-ring diamine platinum(II) and platinum(IV) complexes useful as pharmaceutical agents, to methods for their production, to pharmaceutical compositions which include these compounds and a pharmaceutically acceptable carrier, and to a pharmaceutical method of treatment. More particularly, the novel complexes of the present invention are active against the L1210 murine leukemia cell lines, thus inhibiting the growth of malignant neoplasms in mammals.

Various platinum compounds have been shown to possess antitumor activity. This has been highlighted by the clinical utility of cisplatin (A)

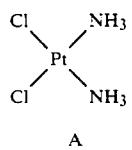

A in the treatment of human tumors. However, because of the severe toxicity, especially nephrotoxicity, associated with the therapeutic use of cisplatin, a number of additional platinum(II) and platinum(IV) analogs have been synthesized and evaluated for antitumor activity. Thus, U.S. Pat. No. 4,477,387 (hereinafter the '387 patent) discloses "platinum(II) complexes represented by the general formula:

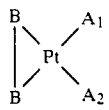

wherein —B—B— is

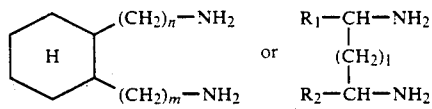

(in which $R_1$ and $R_2$ are the same or different and each is hydrogen, an alkyl group or an aryl group, and n, m and l are 0 or is an integer of from 1 to 3), at least one of $A_1$ and $A_2$ is

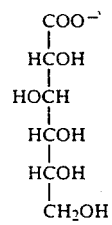

(hereinafter referred to as a ligand of D-gluconic acid) and the other is the ligand of D-gluconic acid, $Cl^-$, $Br^-$, $I^-$, $F^-$, $XCH_2COO^-$ (in which X is a halogen atom), $NO_3^-$, $SO_4^{--}$, $H_2PO_4^-$ or $H_2O$ or, when taken together, $A_1$ and $A_2$ may form a ring together with Pt(II), in the latter case —$A_1$—$A_2$— being the ligand of D-gluconic acid" which have antineoplastic activity.

European Patent Application 0 282,672 (hereinafter the '672 patent application) discloses platinum(II) complexes having antitumor effects and are represented by the formula:

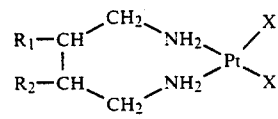

wherein $R_1$ and $R_2$ are each a lower alkyl group; and the two X's are each a halogen atom or jointly form a group represented by

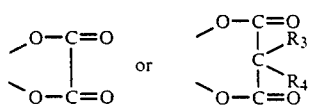

wherein $R_3$ and $R_4$ are each a hydrogen atom or a lower alkyl group; or a group represented by

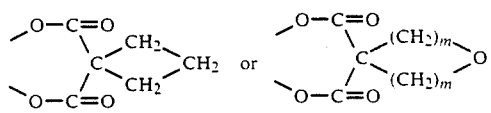

wherein m is 1 or 2.

However, the previous complexes of platinum(II) do not disclose nor suggest the complexes of the present invention. Thus, the '387 patent discloses complexes in which the diamine ligand may be a five to an eleven membered ring. However, rings greater than six members were not exemplified and not characterized by analysis or biological test results. Additionally, all the platinum(II) complexes of the '387 patent contained at least one D-gluconic acid ligand. The '672 patent application discloses only seven membered ring complexes. Thus, we have found unexpectedly that platinum(II) and platinum(IV) complexes in which the diamine ligand is an eight to twelve membered ring have antineoplastic activity.

SUMMARY OF THE INVENTION

Accordingly, a first aspect of the present invention is a neutral mixed-ligand platinum(II) complex of Formula I

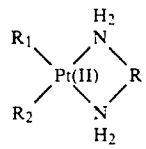

or a pharmaceutically acceptable acid addition salt thereof, wherein R is

in which $R_3$ and $R_4$ are hydrogen, an alkyl group of from one to four carbon atoms, hydroxy, $-CO_2R_5$, in which $R_5$ is an alkyl group of from one to four carbon atoms and n is an integer from five to nine, $-(CH_2)_{1+m}-NHCO-(CH_2)_{1+m1}-CONH-(CH_2)_{1+m2}-$, in which m, $m^1$ and $m^2$ are zero or an integer from one to two and $m+m^1+m^2$ does not exceed two, $-(CH_2)_{1+o}-NHCO-(CH_2)_{1+o1}-$, in which one of o or $o^1$ is zero and the other is an integer from one to five and $o+o^1$ does not exceed five, $-(CH_2)_{1+p}-O-(CH_2)_{1+p1}-O-(CH_2)_{1+p2}-$, in which p, $p^1$ and $p^2$ are zero or an integer from one to four and $p+p^1+p^2$ does not exceed four,

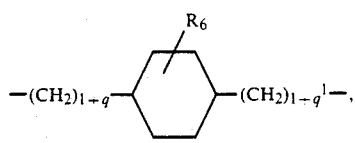

in which q and $q^1$ are zero or an integer from one to three and $q+q^1$ does not exceed three and $R_6$ is
hydrogen,
carboxyl,
an alkyl group of from one to four carbon atoms,
an alkyl group of from one to four carbon atoms substituted with alkoxy of from one to four carbon atoms,
a cycloalkyl group of from three to six carbon atoms,
a hydroxyalkyl group of from one to four carbon atoms,
an alkoxy group of from one to four carbon atoms, or
benzyl,

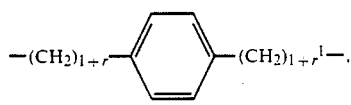

in which r or $r^1$ are zero or an integer from one to three and $r+r^1$ does not exceed three, or

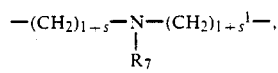

in which s and $s^1$ are an integer from one to six and $s+s^1$ does not exceed six, and $R_7$ is $-CO-R_5$, wherein $R_5$ is as defined above or $-SO_2R_8$ is

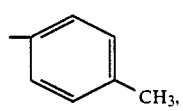

$-CH_3$ or $CF_3$; and and $R_1$ and $R_2$ are negatively charged monodentate ligands which may be the same or different and are selected from the group consisting of chloro, bromo, iodo, nitrato, and acetato or $R_1$ and $R_2$ taken together form a dinegatively charged bidentate ligand selected from the group consisting of sulfato, oxalato,

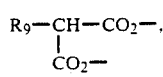

in which $R_9$ is hydrogen, hydroxyl, amino, an alkyl group of from one to four carbon atoms, or an aminoalkyl group of from one to four carbon atoms,

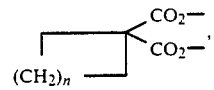

in which n is an integer from one to three, and

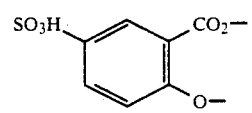

A second aspect of the present invention is a neutral mixed-ligand platinum(IV) complex of Formula II

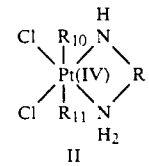

II or a pharmaceutically acceptable acid addition salt thereof, wherein R is

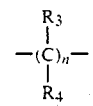

in which $R_3$ and $R_4$ are hydrogen, an alkyl group of from one to four carbon atoms, hydroxy, $-CO_2R_5$, in which $R_5$ is an alkyl group of from one to four carbon atoms and n is an integer from five to nine, $-(CH_2)_{1+m}-NHCO-(CH_2)_{1+m1}-CONH-(CH_2)_{1+m2}-$, in which m, $m^1$ and $m^2$ are zero or an integer from one to two and $m+m^1+m^2$ does not exceed two, $-(CH_2)_{1+o}-NHCO-(CH_2)_{1+o1}-$, in which one of o or $o^1$ is zero and the other is an integer from one to five and $o+o^1$ does not exceed five, $-(CH_2)_{1+p}-O-(CH_2)_{1+p1}-O-(CH_2)_{1+p2}-$, in which p, $p^1$ and $p^2$ are zero or an integer from one to four and $p+p^1+p^2$ does not exceed four,

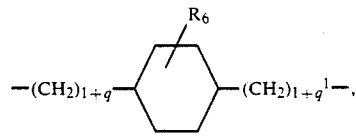

in which q and $q^1$ are zero or an integer from one to three and $q+q^1$ does not exceed three and $R_6$ is
hydrogen,
carboxyl,
an alkyl group of from one to four carbon atoms,
an alkyl group of from one to four carbon atoms substituted with alkoxy of from one to four carbon atoms,
a cycloalkyl group of from three to six carbon atoms,
a hydroxyalkyl group of from one to four carbon atoms, an alkoxy group of from one to four carbon atoms, or benzyl;

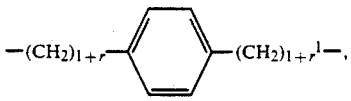

in which r and r¹ are zero or an integer from one to three and r+r¹ does not exceed three, or

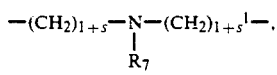

in which s and s¹ are an integer from one to six and s+s¹ does not exceed six and $R_7$ is —CO—$R_5$, wherein $R_5$ is as defined above or $SO_2R_8$ is

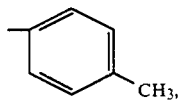

—CH₃ or CF₃; and $R_{10}$ and $R_{11}$ are negatively charged monodentate ligands which may be the same or different and are selected from the group consisting of chloro, bromo, hydroxyl, nitrato, and

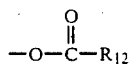

wherein $R_{12}$ is an alkyl group of from one to four carbon atoms.

Additionally, the present invention is directed to a pharmaceutical composition for inhibiting the growth of neoplasms in mammals comprising an antineoplastically effective amount of a neutral mixed ligand platinum(II) complex of Formula I as defined above in combination with a pharmaceutically acceptable carrier.

Also, the present invention is directed to a novel method of inhibiting the growth of neoplasms in mammals comprising administering to said mammal an effective amount of a neutral mixed-ligand platinum(II) complex of Formula I as defined above in combination with a pharmaceutically acceptable carrier.

Further, the present invention is directed to a pharmaceutical composition for inhibiting the growth of neoplasms in mammals comprising an antineoplastically effective amount of a neutral mixed-ligand platinum-(IV) complex of Formula II as defined above in combination with a pharmaceutically acceptable carrier.

Also, the present invention is directed to a novel method of inhibiting the growth of neoplasms in mammals comprising administering to said mammal an effective amount of a neutral mixed-ligand platinum(IV) complex of Formula II as defined above in combination with a pharmaceutically acceptable carrier.

Finally, the present invention is directed to methods for production of compounds of Formula I and Formula II as defined above.

DETAILED DESCRIPTION OF THE INVENTION

In the compounds of Formula I and Formula II, the term "alkyl" means a straight or branched hydrocarbon group having from one to four carbon atoms and includes, for example, methyl, ethyl, n-propyl, isopropyl, n-butyl, isobutyl, tertiary-butyl, and the like.

"Alkoxy" is O-alkyl in which alkyl is as defined above.

"Cycloalkyl" means a saturated hydrocarbon ring having three to six carbon atoms and includes cyclopropyl, cyclobutyl, cyclopentyl, cyclohexyl, and the like.

"Halogen" is iodine, bromine, and chlorine.

Certain of the complexes of Formula I and Formula II which contain basic groups are capable of further forming pharmaceutically acceptable acid addition salts. These forms are within the scope of the present invention.

Pharmaceutically acceptable acid addition salts are formed with inorganic and organic acids, such as, for example, hydrochloric, sulfuric, phosphoric, acetic, citric, gluconic, fumaric, methanesulfonic, and the like (see, for example, Berge, S. M., et al., "Pharmaceutical Salts," *Journal of Pharmaceutical Science*, 66, pp. 1-19 (1977). The acid addition salts of said basic complexes are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Complexes of Formula I and Formula II may also possess asymmetric carbon atoms (optical centers), and thus the racemates as well as the individual enantiomers are also included.

A preferred group of neutral mixed-ligand platinum-(II) complexes are those of Formula I wherein R is

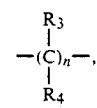

in which $R_3$ and $R_4$ are hydrogen, an alkyl group of from one to four carbon atoms, hydroxy, —$CO_2R_5$, in which $R_5$ is an alkyl group of from one to four carbon atoms and n is an integer from six to nine, —(CH₂)₁₊ₘ—NHCO—(CH₂)₁₊ₘ₁—CONH—(CH₂)₁₊ₘ₂—, in which m, m¹ and m² are zero or an integer from one to two and m+m¹+m² does not exceed two, —(CH₂)₁₊ₒ—NHCO—(CH₂)₁₊ₒ₁—, in which one of o or o¹ is zero and the other is an integer from one to five and o+o¹ does not exceed five, —(CH₂)₁₊ₚ—O—(CH₂)₁₊ₚ₁—O—(CH₂)₁₊ₚ₂—, in which p, p¹ and p² are zero or an integer from one to four and p+p¹+p² does not exceed four,

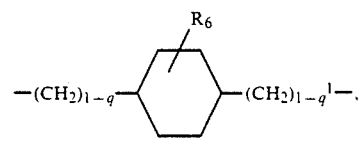

in which q and q¹ are zero or an integer from one to three and q+q¹ does not exceed three and $R_6$ is hydrogen, carboxyl, an alkyl group of from one to four carbon atoms,
an alkyl group of from one to four carbon atoms substituted with alkoxy of from one to four carbon atoms,
a cycloalkyl group of from three to six carbon atoms,
a hydroxyalkyl group of from one to four carbon atoms,
an alkoxy group of from one to four carbon atoms, or benzyl,

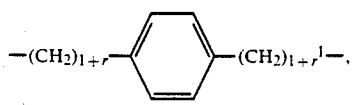

in which r and $r^1$ are zero or an integer from one to three and $r+r^1$ does not exceed three, or

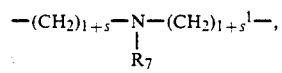

in which s and $s^1$ are an integer from one to six and $s+s^1$ does not exceed six and $R_7$ is $-CO-R_5$, wherein $R_5$ is as defined above or $-SO_2R_8$, wherein $R_8$ is

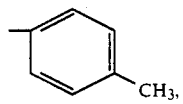

$-CH_3$ or $CF_3$; and $R_1$ and $R_2$ are negatively charged monodentate ligands which may be the same or different and are selected from the group consisting of chloro, bromo, iodo, nitrato, and acetato or $R_1$ and $R_2$ taken together form a dinegatively charged bidentate ligand selected from the group consisting of sulfato, oxalato,

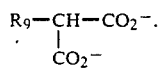

in which $R_9$ is hydrogen, hydroxyl, amino, an alkyl group of from one to four carbon atoms or an aminoalkyl group of from one to four carbon atoms,

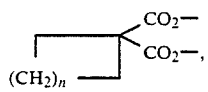

in which n is an integer from one to three, and

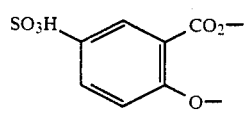

A more preferred group of neutral mixed-ligand platinum(II) complexes are those of Formula I wherein R is

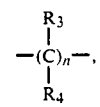

in which $R_3$ and $R_4$ are hydrogen, an alkyl group of from one to four carbon atoms, hydroxy, $-CO_2R_5$, in which $R_5$ is an alkyl group of from one to four carbon atoms and n is an integer from six to nine; and $R_1$ and $R_2$ are negatively charged monodentate ligands which may be the same or different and are selected from the group consisting of chloro and bromo or $R_1$ and $R_2$ taken together form a dinegatively charged bidentate ligand selected from the group consisting of

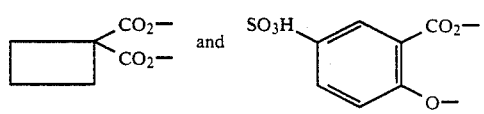

A most preferred group of neutral mixed-ligand platinum(II) complexes are those of Formula I wherein R is $-(CH_2)_n-$, wherein n is an integer from six to nine. Particularly valuable are:
(SP-4-2)-dichloro (1,5-pentanediamine-N,N')platinum;
(SP-4-2)-dichloro (1,6-hexanediamine-N,N')platinum; and
(SP-4-2)-dichloro (1,7-heptanediamine-N,N')platinum.

A preferred group of neutral mixed-ligand platinum-(IV) complexes are those of Formula II wherein R is

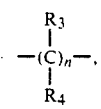

in which $R_3$ and $R_4$ are hydrogen, an alkyl group of from one to four carbon atoms, hydroxy, $-CO_2R_5$, in which $R_5$ is an alkyl group of form one to four carbon atoms and n is an integer from six to nine $-(CH_2)_{1+m}-NHCO-(CH_2)_{1+m1}-CONH-(CH_2)_{1+m2}-$, in which m, $m^1$ and $m^2$ are zero or an integer from one to two and $m+m^1+m^2$ does not exceed two, $-(CH_2)_{1+o}-NHCO-(CH_2)_{1+o1}-$, in which one of o or $o^1$ is zero and the other is an integer from one to five and $o+o^1$ does not exceed five, $-(CH_2)_{1+p}-O-(CH_2)_{1+p1}-O-(CH_2)_{1+p2}-$, in which p, $p^1$ and $p^2$ are zero or an integer from one to four and $p+p^1+p^2$ does not exceed four,

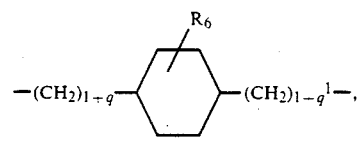

in which q and $q^1$ are zero or an integer from one to three and $q+q^1$ does not exceed three and $R_6$ is
hydrogen,
carboxyl,
an alkyl group of from one to four carbon atoms,
an alkyl group of from one to four carbon atoms substituted with alkoxy of from one to four carbon atoms,
a cycloalkyl group of from three to six carbon atoms,
a hydroxyalkyl group of from one to four carbon atoms, an alkoxy group of from one to four carbon atoms, or benzyl, in which r and $r^1$ are zero or an integer from one to three and $r+r^1$ does not exceed three, or

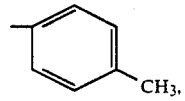

in which s and $s^1$ are an integer from one to six and $s+s^1$ does not exceed six and $R_7$ is —CO—$R_5$, wherein $R_5$ is as defined above or —$SO_2R_8$, wherein $R_8$ is

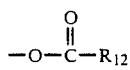

—$CH_3$ or $CF_3$; and $R_{10}$ and $R_{11}$ are negatively charged monodentate ligands which may be the same of different and are selected from the group consisting of chloro, bromo, hydroxyl, nitrato, and

wherein $R_{12}$ is an alkyl group of from one to four carbon atoms.

A more preferred group of neutral mixed-ligand platinum(IV) complexes are those of Formula II wherein R is

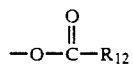

in which $R_3$ and $R_4$ are hydrogen, an alkyl group of from one to four carbon atoms, hydroxy, —$CO_2R_5$, in which $R_5$ is an alkyl group of from one to four carbon atoms and n is an integer from six to nine; and $R_{10}$ and $R_{11}$ are negatively charged monodentate ligands which may be the same of different and are selected from the group consisting of chloro, bromo, hydroxyl, nitrato, and

—O—C(=O)—$R_{12}$ wherein $R_{12}$ is an alkyl group of from one to four carbon atoms.

A most preferred group of neutral mixed-ligand platinum(IV) complexes are those of Formula II wherein R is —$(CH_2)_n$—, wherein n is an integer from six to nine.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The process of preparing neutral mixed-ligand platinum(II) complexes of Formula I is described generally as follows:

A neutral mixed-ligand platinum(II) complex of Formula I

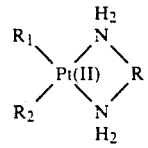

or a pharmaceutically acceptable acid addition salt thereof, wherein R is

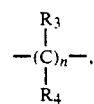

in which $R_3$ and $R_4$ are hydrogen, an alkyl group of from one to four carbon atoms, hydroxy, —$CO_2R_5$, in which $R_5$ is an alkyl group of from one to four carbon atoms and n is an integer from five to nine, —$(CH_2)_{1+m}$—NHCO—$(CH_2)_{1+m1}$—CONH—$(CH_2)_{1+m2}$—, in which m, $m^1$ and $m^2$ are zero or an integer from one to two and $m+m^1+m^2$ does not exceed two, —$(CH_2)_{1+o}$—NHCO—$(CH_2)_{1+o1}$—, in which one of o or $o^1$ is zero and the other is an integer from one to five and $o+o^1$ does not exceed five, —$(CH_2)_{1+p}$—O—$(CH_2)_{1+p1}$—O—$(CH_2)_{1+p2}$—, in which p, $p^1$ and $p^2$ are zero or an integer from one to four and $p+p^1+p^2$ does not exceed four,

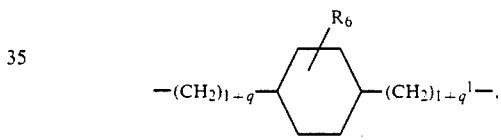

in which q and $q^1$ are zero or an integer from one to three and $q+q^1$ does not exceed three and $R_6$ is
hydrogen,
carboxyl,
an alkyl group of from one to four carbon atoms
an alkyl group of from one to four carbon atoms substituted with alkoxy of from one to four carbon atoms,
a cycloalkyl group of from three to six carbon atoms,
a hydroxyalkyl group of from one to four carbon atoms,
an alkoxy group of from one to four carbon atoms, or benzyl,

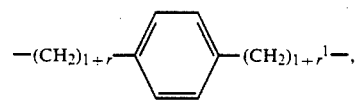

in which r and $r^1$ are zero or an integer from one to three and $r+r^1$ does not exceed three, or

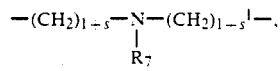

in which s and $s^1$ are an integer from one to six and $s+s^1$ does not exceed six and $R_7$ is —CO—$R_5$, wherein $R_5$ is as defined above or —$SO_2R_8$, wherein $R_8$ is

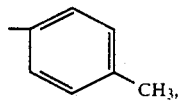

—CH₃ or CF₃; and $R_1$ and $R_2$ are negatively charged monodentate ligands which may be the same or different and are selected from the group consisting of chloro, bromo, iodo, nitrato, and acetato or $R_1$ and $R_2$ taken together form a dinegatively charged bidentate ligand selected from the group consisting of sulfato, oxalato,

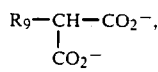

in which $R_9$ is hydrogen, hydroxyl, amino, an alkyl group of from one to four carbon atoms or an aminoalkyl group of from one to four carbon atoms,

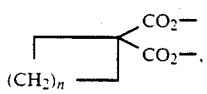

in which n is an integer from one to three, and

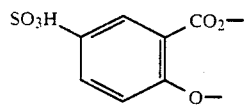

is prepared by reacting a compound of Formula III

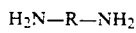   III wherein R is as defined above with potassium tetraiodoplatinate(II) in water at about 60° C. to afford a complex of Formula Ia

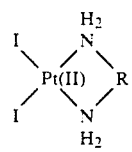   Ia wherein R is as defined above.

Treatment of a complex of Formula Ia in a conventional manner affords a complex of Formula I.

Thus, treatment of the complex of Formula Ia wherein R is as defined above with an aqueous solution of silver nitrate precipitates silver iodide and affords a complex of Formula Ib

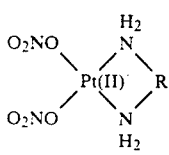   Ib wherein R is as defined above.

Treatment of the complex of Formula Ia wherein R is as defined above with an aqueous solution of silver nitrate precipitates silver iodide followed by filtration and addition of a dilute aqueous solution of hydrochloric acid to the filtrate affords a complex of Formula Ic

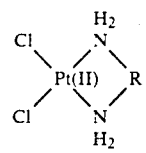   Ic wherein R is as defined above.

Substitution of a dilute aqueous solution of hydrobromic acid for hydrochloric acid in the previous reaction affords a complex of Formula Id

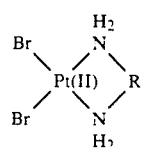   Id wherein R is as defined above.

Substitution of an aqueous buffer solution of sodium acetate/acetic acid (pH 5-6) for hydrochloric acid in the previous reaction affords a complex of Formula Ie

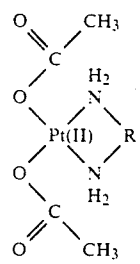   Ie wherein R is as defined above.

Treatment of the complex of Formula Ia wherein R is as defined above with an aqueous solution of silver sulfate precipitates silver iodide and affords a complex of Formula If

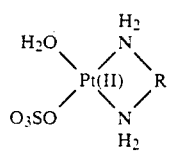   If wherein R is as defined above.

Treatment of the complex of Formula If wherein R is as defined above with a solution of barium hydroxide to remove the sulfate, followed by filtration and reaction with a solution of oxalic acid (pH adjusted to 6 with sodium hydroxide) affords a complex of Formula Ig

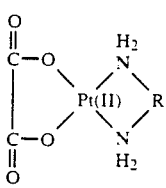   Ig wherein R is as defined above.

Substitution of $$R_9-\underset{\underset{CO_2H}{|}}{CHCO_2H},$$

in which $R_9$ is as defined above, for oxalic acid in the previous reaction affords a complex of Formula Ih Ih

[Structure: $R_9$—CH with two C(=O)—O groups coordinated to Pt(II), which is also coordinated to two $NH_2$ groups bridged by R]

wherein R and $R_9$ are as defined above.

Substitution of

[Structure: $(CH_2)_n$ ring with C bearing two $CO_2H$ groups]

(pH adjusted to 5–6) in which n is as defined above, for the solution of oxalic acid in the previous reaction affords a complex of Formula Ii Ii

[Structure: $(CH_2)_n$ ring with C bearing two C(=O)—O groups coordinated to Pt(II), which is also coordinated to two $NH_2$ groups bridged by R]

wherein R and n are as defined above.

Substitution of

[Structure: benzene ring with $SO_3H$, $CO_2^-$, and $O^-$ substituents]

for oxalic acid in the previous reaction affords a complex of Formula Ij

Ij

[Structure: benzene ring with $HO_3S$ substituent, and with C(=O)—O and O groups coordinated to Pt(II), which is also coordinated to two $NH_2$ groups bridged by R]

wherein R is as defined above.

Potassium tetraiodoplatinate is prepared in situ from potassium tetrachloroplatinate and potassium iodide in the conventional manner.

Compounds of Formula III are either known or capable of being prepared by methods known in the art.

The process of preparing neutral mixed-ligand platinum(IV) complexes of Formula II is described generally as follows:

A neutral mixed-ligand platinum(IV) complex of Formula II

II

[Structure: Pt(IV) coordinated to two Cl, $R_{10}$, $R_{11}$, and two $NH_2$ groups bridged by R]

or a pharmaceutically acceptable acid addition salt thereof, wherein R is $$-\underset{\underset{R_4}{|}}{\overset{\overset{R_3}{|}}{(C)}}{}_n-,$$

in which $R_3$ and $R_4$ are hydrogen, an alkyl group of from one to four carbon atoms, hydroxy, $-CO_2R_5$, in which $R_5$ is an alkyl group of from one to four carbon atoms and n is an integer from five to nine, $-(CH_2)_{1+m}-NHCO-(CH_2)_{1+m1}-CONH-(CH_2)_{1+m2}-$, in which m, $m^1$ and $m^2$ are zero or an integer from one to two and $m+m^1+m^2$ does not exceed two, $-(CH_2)_{1+o}-NHCO-(CH_2)_{1+o1}-$, in which one of o or $o^1$ is zero and the other is an integer from one to five and $o+o^1$ does not exceed five, $-(CH_2)_{1+p}-O-(CH_2)_{1+p1}-O-(CH_2)_{1+p2}-$, in which p, $p^1$ and $p^2$ are zero or an integer from one to four and $p+p^1+p^2$ does not exceed four,

[Structure: $-(CH_2)_{1-q}-$ cyclohexyl with $R_6$ substituent $-(CH_2)_{1-q^1}-$]

in which q and $q^1$ are zero or an integer from one to three and $q+q^1$ does not exceed three and $R_6$ is hydrogen, carboxyl, an alkyl group of from one to four carbon atoms, an alkyl group of from one to four carbon atoms substituted with alkoxy of from one to four carbon atoms, a cycloalkyl group of from three to six carbon atoms, a hydroxyalkyl group of from one to four carbon atoms, an alkoxy group of from one to four carbon atoms, or benzyl,

[Structure: $-(CH_2)_{1+r}-$ phenyl $-(CH_2)_{1-r^1}-$]

in which r and $r^1$ are zero or an integer from one to three and $r+r^1$ does not exceed three, or $$-(CH_2)_{1-s}-\underset{\underset{R_7}{|}}{N}-(CH_2)_{1-s^1}-.$$

in which s and $s^1$ are an integer from one to six and $s+s^1$ does not exceed six and $R_7$ is $-CO-R_5$, wherein $R_5$ is as defined above or $-SO_2R_8$, wherein $R_8$ is

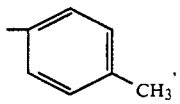

CH₃ or CF₃; and $R_{10}$ and $R_{11}$ are negatively charged monodentate ligands which may be the same or different and are selected from the group consisting of chloro, bromo, hydroxyl, nitrato, and

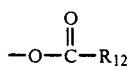

wherein $R_{12}$ is an alkyl group of from one to four carbon atoms, is prepared by reacting a complex of Formula Ic.

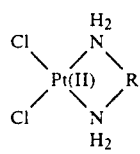

Ic wherein R is as defined above.

Treatment of a complex of Formula Ic in a conventional manner affords a complex of Formula II. Thus, treatment of a complex of Formula Ic in a 15% aqueous solution of hydrogen peroxide and concentrated hydrochloric acid solution at about room temperature to about 60° C. affords a complex of Formula IIa

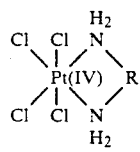

IIa wherein R is as defined above.

Treatment of the complex of Formula Ic wherein R is as defined above in water with a 15% aqueous solution of hydrogen peroxide while warming at about room temperature to about 60° C. affords a complex of Formula IIb

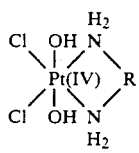

IIb wherein R is as defined above.

Treatment of the complex of Formula IIb wherein R is as defined above in water with an aqueous solution of nitric acid affords a complex of Formula IIc

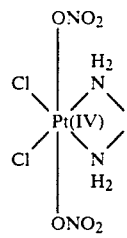

IIc wherein R is as defined above.

The neutral mixed-ligand platinum II complexes of Formula I and platinum IV complexes of Formula II can be prepared and administered in a wide variety of oral and parenteral dosage forms. The complexes of Formula I and Formula II are valuable anticancer agents.

The data in Table 1 shows the antineoplastic activity of representative compounds of the present invention. Thus, in Table 1, the efficacy of Example 1 and 2 of the present invention compared to [SP-4-2-(1R-trans)]-dichloro(1,2-cyclohexanediamine-N,N′)platinum[Pt(-trans-l-DACH)Cl₂] is shown as measured against strains of L1210 cell lines which were selected for their resistance to cis-diaminedichloroplatinum(II) (cisplatin). $ID_{50}$ values were determined for each compound shown in the table as measured against the normal L1210 cell line, as well as against the L1210 cell line which was selected for its resistance to cisplatin at a concentration of 4 μg/ml. $ID_{50}$ values are the concentration of complex required to inhibit the in vitro growth of treated cells to a level of 50% of that for untreated cells over a 72-hour period. The cell lines are suspended in appropriate media at a concentration which results in the cells remaining in log phase growth throughout the treatment period. Serially diluted drug is added to duplicate wells containing the cell growth. After 72 hours of incubation of the cell lines in 5% $CO_2$, the cells are counted and the $ID_{50}$ values determined.

Resistance ratio values shown in Table 1 were calculated by dividing the $ID_{50}$ values against the resistant cell lines by the $ID_{50}$ values against the normal cell lines. The resistance ratio values shown in the table indicate a measure of the degree of resistance of the cell line to a particular drug. Thus, the higher the resistance ratio, the less effective is the drug against the cisplatin-resistant cell line.

Moreover, the complexes of the present invention demonstrate activity the L1210 murine leukemia cell line. The screening tests employing these cell lines are described in Geran et al., "Protocols for Screening Chemical Agents and Natural Products Against Animal Tumors and Other Biological Systems," *Cancer Chemotherapy Reports*, Part 3, Vol. 3, No. 2, pages 1–85 (1972). The L1210 screening method has been cited as the best tool for predicting clinical utility of drugs in the treatment of human solid tumors as well as human leukemias and lymphomas (Venditti, "Relevance of Transplantable Animal-Tumor Systems to the Selection of New Agents for Clinical Trial," Pharmacological Basis of Cancer Chemotherapy, Williams & Williams Pub. Co. (1975)).

The antitumor activity of Example 1 and Example 2 are superior to cisplatin both in potency and response according to in vitro test results. While Example 1 and Example 2 show some degree of cross resistance to cisplatin in vitro, they are more effective than cisplatin against cisplatin-resistant cells in vitro. Additionally, Example 1 and Example 2 show only a 2.7 and 2.3 fold respectively cross resistance to Pt(DACH)Cl$_2$-resistant L1210 cells in culture while [Pt(trans-1-DACH)Cl$_2$] shows a 30-fold resistance to the same system.

TABLE 1

In Vitro Cytotoxicity of Compounds of the Present Invention, ID$_{50}$ (μg/ml)

| Cell Line | Cisplatin | [Pt(trans-l-DACH)Cl$_2$]$^a$ | Example 1 | Example 2 |
|---|---|---|---|---|
| L1210S | 0.34 (1)$^b$ | 0.088 (1) | 0.43 (1) | 0.93 (1) |
| L1210PtR4 | 3.61 (11) | 0.159 (1.8) | 1.13 (2.6) | 2.8 (3) |
| L1210DDP5 | 5.63 (16) | 0.176 (2) | 1.58 (3.7) | 3.7 (4) |
| L1210DACH | 0.467 (1.4) | 2.67 (30) | 1.17 (2.7) | 2.13 (2.3) |

$^a$[SP-4-2-(1R-trans)]-dichloro(1,2-cyclohexanediamine-N,N')platinum.
$^b$numbers in parentheses are factors of cross-resistance.

For preparing pharmaceutical compositions from the complexes of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from 5 to 10 to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can also be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg, preferably 1 mg to 10 mg, according to the particular application and the potency of the active component. The composition can, if desired, also contain other compatible therapeutic agents.

In therapeutic use as antineoplastic agents, the complexes utilized in the pharmaceutical method of this invention are administered to the patient preferably in daily intravenous doses of from 10 to 100 mg/m$^2$ of body area on a regimen of from one to seven days, repeated as needed after a hiatus of from two to six weeks. The dosages and dosage regimen, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred method for preparing the complexes of the invention.

EXAMPLE 1

(SP-4-2)-Dichloro(1,5-pentanediamine-N,N')-platinum

A solution of potassium tetraiodoplatinate(II), 400 ml (prepared in situ from 5 g (12 mmol) of potassium tetrachloroplatinate in 350 ml of water and 14.62 g (88.1 mmol) of potassium iodide in 50 ml of water) and 1.06 g of 1,5-pentanediamine in 400 ml of water are simultaneously pumped at equal rates (2.6 ml/minute) via a peristalic pump into a 3-liter flask containing 250 ml of water maintained at 60° C. The flask is stirred vigorously via an external mechanical stirrer as the reagents are delivered over a 1.9 to 4.76 hour period. The reaction mixture is maintained at 60° C. during delivery of the reagents and for 0.5 to 1 hour after delivery. The reaction is cooled to ambient temperature, filtered through a medium porosity sintered glass filter (material adhering to the inside surface of the reaction flask is loosened via agitation in an ultrasonic bath) to afford about 5.7 g of the iodoamine intermediate. The iodoamine intermediate is slurried in water. Following the addition of silver nitrate solution (110% of the stoichmetric amount) to this slurry, the resultant mixture is heated at 60° C. with stirring for 30 to 60 minutes; allowed to stir at ambient temperature overnight, filtered (0.2 μ filter) to afford a clear water while filtrate. Excess silver cation is removed as silver chloride via several additions (followed by filtration after each addition) of 1 M hydrochloric acid. The silver-free filtrate (300 to 400 ml) is cooled to 0° C., concentrated in vacuo to about 50 ml, 4 ml (48 mmol) of 12 N hydrochloric acid (twice the stoichiometric amount of $Cl^-$ ion) is added, the mixture warmed to about 45° C. for 15 minutes, and then cooled in an ice bath to crystallize the desired product. The pale yellow compound obtained was filtered, washed with 0.1 N hydrochloric acid (0° C.) and ethanol (0° C.), dried by suction in air, and then in vacuo at 50° C. for two hours to afford 0.043 g of (SP-4-2)-dichloro(1,5-pentanediamine-N,N')-platinum.

Anal. for
Calc.: C, 16.31; H, 3.83; N, 7.61; Cl, 19.16;
Found: C, 16.42; H, 3.76; N, 7.62; Cl, 19.09.
$^{195}$Pt-NMR (nuclear magnetic resonance) (Dimethylformamide-$d_7$)(DMF-$d_7$) ppm )parts per million): 493.7;
$^{13}$C-NMR (DMF-$d_7$) ppm: 21.95; 27.42; 44.26;
MS(FAB) (mass spectrum—fast atom bombardment spectrum) molecular ion 368.0.

EXAMPLE 2

(SP-4-2)-Dichloro(1,6-hexanediamine-N,N')-platinum

A solution of potassium tetraiodomplatinate(II), 400 ml (prepared in situ from 5 g (12 mmol) of potassium tetrachloroplatinate in 350 ml of water and 14.62 g (88.1 mmol) of potassium iodide in 50 ml of water) and 1.395 g of 1,6-hexanediamine in 400 ml of water are simultaneously pumped at equal rates (2.6 ml/minute) via a peristalic pump into a 3-liter flask containing 250 ml of water maintained at 60° C. The flask is stirred vigorously via an external mechanical stirrer as the reagents are delivered over a 1.9 to 4.76 hour period. The reaction mixture is maintained at 60° C. during delivery of the reagents and for 0.5 to 1 hour after delivery. The reaction is cooled to ambient temperature, filtered through a medium porosity sintered glass filter (material adhering to the inside surface of the reaction flask is loosened via agitation in an ultrasonic bath) to afford about 5.7 g of the iodoamine intermediate. The iodoamine intermediate is slurried in water. Following the addition of silver nitrate solution (110% of the stoichmetric amount) to this slurry, the resultant mixture is heated at 60° C. with stirring for 30 to 60 minutes, allowed to stir at ambient temperature overnight, filtered (0.2 μ filter) to afford a clear, water white filtrate. Excess silver cation is removed as silver chloride via several additions (followed by filtration after each addition) of 1 M hydrochloric acid. The silver-free filtrate (300 to 400 ml) is cooled to 0° C.. concentrated in vacuo to about 50 ml, 4 ml (48 mmol) of 12 N hydrochloric acid (twice the stoichiometric amount of $Cl^-$ ion) is added, the mixture warmed to about 45° C. for 15 minutes, and then cooled in an ice bath to crystallize the desired product. The pale yellow compound obtained was filtered, washed with 0.1 N hydrochloric acid (0° C.) and ethanol (0° C.), dried by suction in air, and then in vacuo at 50° C. for two hours to afford 0.055 g of product. Recrystallization affords 0.043 g of (SP-4-2)-dichloro (1,6-hexanediamine-N,N')-platinum Anal. for
Calc.: C, 18.86; H, 4.22; N, 7.33;
Found: C, 18.93; H, 4.29; N, 7.30.
$^{195}$Pt-NMR (DMF-$d_7$) ppm:590.1;
$^{13}$C-NMR (DMF-$d_7$) ppm:26.47; 31.04; 47.36;
MS(FAB) molecular ion 382

EXAMPLE 3

(SP-4-2)-Dichloro(1,7-heptanediamine-N,N')-platinum

A solution of potassium tetraiodoplatinate(II), 400 ml (prepared in situ from 5 g (12 mmol) of potassium tetrachloroplatinate in 350 ml of water and 14.62 g (88.1 mmol) of potassium iodide in 50 ml of water) and 1.395 g of 1,7-heptanediamine in 400 ml of water are simultaneously pumped at equal rates (1.4 ml/minute) via a peristalic pump into a 3-liter flask containing 250 ml of water maintained at 60° C. The flask is stirred vigorously via an external mechanical stirrer as the reagents are delivered over a 1.9 to 4.76 hour period. The reaction mixture is maintained at 60° C. during delivery of the reagents and for 0.5 to 1 hour after delivery. The reaction is cooled to ambient temperature, filtered through a medium porosity sintered glass filter (material adhering to the inside surface of the reaction flask is loosened via agitation in an ultrasonic bath) to afford about 5.7 g of the iodoamine intermediate. The iodoamine intermediate is slurried in water. Following the addition of silver nitrate solution (110% of the stoichmetric amount) to this slurry, the resultant mixture is heated at 60° C. with stirring for 30 to 60 minutes, allowed to stir at ambient temperature overnight, filtered (0.2 μ filter) to afford a clear, water white filtrate. Excess silver cation is removed as silver chloride via several additions (followed by filtration after each addition) of 1 M hydrochloric acid. The silver-free filtrate (300 to 400 ml) is cooled to 0° C., concentrated in vacuo to about 50 ml, 4 ml (48 mmol) of 12 N hydrochloric acid (twice the stoichiometric amount of $Cl^-$ ion) is added, the mixture warmed to about 45° C. for 15 minutes, and then cooled in an ice bath to crystallize the desired product. The pale yellow compound obtained was filtered, washed with 0.1 N hydrochloric acid (0° C.) and ethanol (0° C.), dried by suction in air, and then in vacuo at 50° C. for two hours to afford 0.088 g of product. Recrystallization from dimethylformamide: hydrochloric acid affords 30 mg of (SP-4-2)-dichloro (1,7-heptanediamine-N,N')-platinum Anal. for
Calc.: C, 21.22; H, 4.58; N, 7.07;
Found: C, 21.37; H, 4.79; N, 7.06.

I claim:

1. A neutral mixed-ligand platinum(II) complex of Formula I

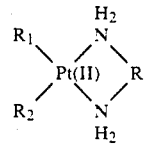

or a pharmaceutically acceptable acid addition salt thereof, wherein R is

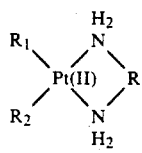

in which $R_3$ and $R_4$ are hydrogen, or an alkyl group of from one to four carbon atoms and n is an integer from five to nine and $R_1$ and $R_2$ are negatively charged monodentate ligands which may be the same or different and are selected from the group consisting of chloro, bromo, iodo, nitrato, and acetato or $R_1$ and $R_2$ taken together form a dinegatively charged bidentate ligand selected from the group consisting of sulfato, oxalato,

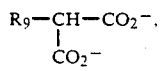

in which $R_9$ is hydrogen or alkyl group of from one to four carbon atoms.

2. A neutral mixed-ligand platinum(IV) complex of Formula II

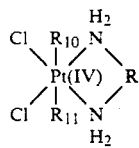

or a pharmaceutically acceptable acid addition salt thereof, wherein R is

in which $R_3$ and $R_4$ are hydrogen, or an alkyl group of from one to four carbon atoms and n is an integer from five to nine and $R_{10}$ and $R_{11}$ are negatively charged monodentate ligands which may be the same or different and are selected from the group consisting of chloro, bromo, hydroxyl, nitrato, and $$-O-\overset{O}{\underset{\|}{C}}-R_{12}$$

wherein $R_{12}$ is an alkyl group of from one to four carbon atoms.

3. A neutral mixed-ligand platinum(II) complex as defined in claim 1 wherein R is

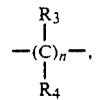

in which $R_3$ and $R_4$ are hydrogen, or an alkyl group of from one to four carbon atoms and n is an integer from six to nine and $R_1$ and $R_2$ are negatively charged monodentate ligands which may be the same or different and are selected from the group consisting of chloro, bromo, iodo, nitrato, and acetato or $R_1$ and $R_2$ taken together form a dinegatively charged bidentate ligand selected from the group consisting of sulfato, oxalato,

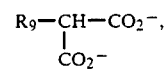

in which $R_9$ is hydrogen, or alkyl group of from one to four carbon atoms.

4. A neutral mixed-ligand platinum(II) complex as defined in claim 3 wherein R is

in which $R_3$ and $R_4$ are hydrogen, an alkyl group of from one to four carbon atoms and n is an integer from six to nine; and $R_1$ and $R_2$ are negatively charged monodentate ligands which may be the same or different and are selected from the group consisting of chloro and bromo.

5. A neutral mixed-ligand platinum(II) complex as defined in claim 4 wherein R is $-(CH_2)_n-$, wherein n is an integer from six to nine.

6. A neutral mixed-ligand platinum(IV) complex as defined in claim 2 wherein R is

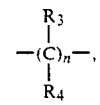

in which $R_3$ and $R_4$ are hydrogen, or an alkyl group of from one to four carbon atoms and n is an integer from six to nine and $R_{10}$ and $R_{11}$ are negatively charged monodentate ligands which may be the same or different and are selected from the group consisting of chloro, bromo, hydroxyl, nitrato, and $$-O-\overset{O}{\underset{\|}{C}}-R_{12}$$

wherein $R_{12}$ is an alkyl group of from one to four carbon atoms.

7. A neutral mixed-ligand platinum(IV) complex as defined in claim 6 wherein R is

in which $R_3$ and $R_4$ are hydrogen, or an alkyl group of from one to four carbon atoms and n is an integer from six to nine; and $R_{10}$ and $R_{11}$ are negatively charged monodentate ligands which may be the same of different and are selected from the group consisting of chloro, bromo, hydroxyl, nitrato, and

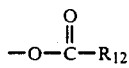

wherein $R_{12}$ is an alkyl group of from one to four carbon atoms.

8. A neutral mixed-ligand platinum(IV) complex as defined in claim 7 wherein R is $-(CH_2)_n-$, wherein n is an integer from six to nine.

9. A neutral mixed-ligand platinum(II) complex as defined in claim 1 having the name (SP-4-2)dichloro(1,5)-pentanediamine-N,$N^1$)-platinum.

10. A neutral mixed-ligand platinum(II) complex as defined in claim 1 having the same (SP-4-2)dichloro(1,6-hexanediamine-N,$N^1$)-platinum.

11. A neutral mixed-ligand platinum(II) complex as defined in claim 1 having the name (SP-4-2)dichloro(1,7-heptanediamine-N,$N^1$)-platinum.

12. A pharmaceutical composition for inhibiting the growth of neoplasms in mammals comprising an antineoplastically effective amount of a neutral mixed-ligand platinum(II) complex as defined by claim 1 in combination with a pharmaceutically acceptable carrier.

13. A pharmaceutical composition for inhibiting the growth of neoplasms in mammals comprising an antineoplastically effective amount of a neutral mixed-ligand platinum(IV) complex as defined by claim 2 in combination with a pharmaceutically acceptable carrier.

* * * * *

UNITED STATES PATENT AND TRADEMARK OFFICE
CERTIFICATE OF CORRECTION

PATENT NO. : 5,049,686
DATED : September 17, 1991
INVENTOR(S) : Hoeschele, J. D.

It is certified that error appears in the above-identified patent and that said Letters Patent is hereby corrected as shown below:

In column 21, line 5, delete:

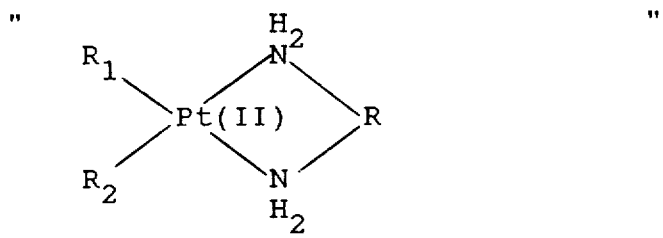

and insert

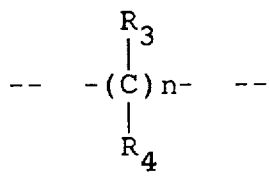

In column 24, line 2, delete "same" and insert -- name --.

Signed and Sealed this

Twenty-third Day of March, 1993

*Attest:*

STEPHEN G. KUNIN

*Attesting Officer*  Acting Commissioner of Patents and Trademarks